US00PP24826P3

(12) United States Plant Patent
Korlipara

(10) Patent No.: US PP24,826 P3
(45) Date of Patent: Aug. 26, 2014

(54) ***COREOPSIS* PLANT NAMED 'SUMMER PUNCH'**

(50) Latin Name: ***Coreopsis* hybrid**
Varietal Denomination: Summer Punch

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 199 days.

(21) Appl. No.: 13/573,503

(22) Filed: Sep. 19, 2012

(65) Prior Publication Data

US 2014/0082804 P1 Mar. 20, 2014

(51) Int. Cl.
*A01H 5/00* (2006.01)

(52) U.S. Cl.
USPC ..... Plt./417

(58) Field of Classification Search
CPC ..... A01H 5/025; A01H 5/02; A01H 5/00
USPC ..... Plt./417
See application file for complete search history.

*Primary Examiner* — June Hwu
(74) *Attorney, Agent, or Firm* — Klarquist Sparkman, LLP

(57) ABSTRACT

A new and distinct *Coreopsis* plant named 'Summer Punch' characterized by large daisy-type flowers that grow to 5.5 cm in diameter, yellow flowers with dark red centers, grass green foliage on strong, upright, short stems, flowering for the whole summer, and excellent vigor.

1 Drawing Sheet

Botanical denomination: *Coreopsis* hybrid.
Variety designation: 'Summer Punch'.

BACKGROUND OF THE INVENTION

The present invention relates to a new and distinct cultivar of *Coreopsis* and given the cultivar name 'Summer Punch'. *Coreopsis* is in the family Asteraceae. This new cultivar originated from an open pollinated cross of picked from unknown proprietary parents in the breeding area for new colors in *Coreopsis*.

Compared to *Coreopsis* 'Route 66' (U.S. Plant Pat. No. 20,609), the new cultivar is shorter and has somewhat darker flowers.

Compared to *Coreopsis tinctoria*, an unpatented plant, the new cultivar has larger flowers and a much shorter habit.

SUMMARY OF THE INVENTION

The following traits have been repeatedly observed and are determined to be the unique characteristics of the new variety. These characteristics in combination distinguish *Coreopsis* 'Summer Punch' as a new and distinct cultivar:

1. large daisy-type flowers that grow to 5.5 cm in diameter,
2. yellow flowers with dark red centers,
3. grass green foliage on strong, upright, short stems,
4. flowering for the whole summer, and
5. excellent vigor.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The photograph shows a one-year-old *Coreopsis* 'Summer Punch' growing in the ground in the trial field in August in Canby, Oreg.

DETAILED PLANT DESCRIPTION

The following is a detailed description of the new *Coreopsis* cultivar based on observations of nine-month-old specimens growing in the ground in full sun under typical outdoor conditions in the garden in June in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on *The Royal Horticultural Society Colour Chart*, $5^{th}$ edition.

Plant:

*Type*.—Herbaceous perennial.
*Hardiness*.—USDA Zone 9.
*Size*.—38 cm wide and 35 cm tall to top of inflorescences.
*Form*.—Upright.
*Vigor*.—Excellent.
*Roots*.—Fibrous, stems root easily from stem cuttings.

Stem:

*Type*.—Ascending.
*Size*.—25 cm tall to where branches for flowering and 10 mm wide at base.
*Number of stems from the crown*.—2-3.
*Internode length*.—2 cm to 6 cm.
*Surface*.—Glabrous.

*Color*.—Yellow Green 146A except at base where tinted Greyed Purple 187B.

Leaf:

*Type*.—Simple.

*Size*.—Grows to 12 cm long and 12 mm wide, usually 4 cm long and 3 mm wide.

*Shape*.—Linear.

*Arrangement*.—Opposite.

*Margins*.—Entire.

*Apex*.—Acute.

*Base*.—Attenuate.

*Venation*.—Pinnate.

*Surface texture*.—Glabrous.

*Petiole*.—None.

*Color*.—Top and bottom side Yellow Green 137C.

Inflorescence:

*Type*.—Long stalked terminal heads of daisy type inflorescences.

*Peduncle*.—16 cm long, 1.5 mm wide, glabrous, Yellow Green 146A.

*Size*.—Grows to 5.5 cm wide and 10 mm deep.

*Immature*.—5.5 mm deep and 7 mm wide, ovoid, glabrous, top ½ Greyed Yellow 161A streaked Greyed Purple 187A; bottom ½ Yellow Green 146A.

*Receptacle*.—Disc shaped, 3 mm wide and 2 mm deep, Yellow Green 146B.

*Phyllary*.—In two series; inner series broadly campanulate with 8 reflexing lobes, grows to 15 mm wide and 6 mm deep, each lobe ovate, margin entire, tip acute, glabrous on both sides, 7 mm long and 4 mm wide; top and bottom side on top ⅔ Yellow Orange 21A tipped and edged with Greyed Purple 187A, bottom ⅓ Yellow Green 146B; outer series stellate, grows to 8 mm wide and 3 mm deep, with 8 lobes, each lobe 3 mm long and 1.5 mm wide, ovate, margin entire, tip acute, both sides glabrous and Green 137B with tips Greyed Purple 187A.

*Lastingness*.—Each inflorescence lasts about a week on the plant.

Florets:

*Type*.—Composite.

*Ray florets*.—8 in number with no pistil or stamen, obovate with the tip three lobed with lobes obtuse and notched and the central lobe the longest and most notched, entire on both sides, grows to 30 mm long, 15 mm wide, glabrous, topside Yellow Orange 13A on the top half and Greyed Purple 187B on the bottom half and margins; bottom side Greyed Yellow 161B with margins and base tinted Greyed Purple 187B.

*Disc*.—Conic, deeper with maturity, 10 mm wide and becoming 6 mm deep with maturity; Greyed Purple 185A.

*Disc florets*.—With stamen and pistil, about 110 in number, 8 mm long and 1.5 mm wide, tubular; corolla 5 mm long and 1.5 mm wide, inside and out tube Yellow Orange 14A, 4 lobes Greyed Purple 185A; pistil 1, ovary 1 mm long, White 155A, style 5 mm long, extruding, with 2-branched stigma, stigma and style Yellow Orange 23C; stamen 5, anthers 2 mm long, Greyed Purple N187A, pollen Yellow 14C.

*Bloom period*.—June through October in Canby, Oreg.

*Fragrance*.—Slight.

*Seed*.—None seen.

*Fertility*.—Infertile.

Disease and pests: The new cultivar is typical to the genus. No known resistances to pests or diseases. No problems have been found in Canby, Oreg.

I claim:

1. A new and distinct *Coreopsis* plant as herein illustrated and described.

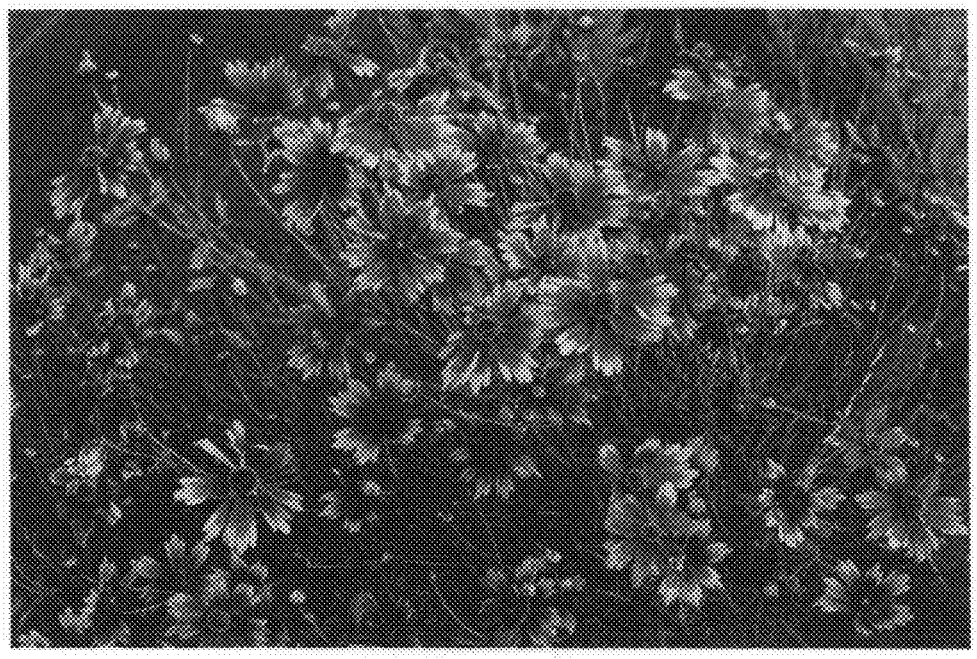

* * * * *